United States Patent [19]
Grodberg

[11] Patent Number: 5,013,728
[45] Date of Patent: May 7, 1991

[54] COMPOSITION FOR TREATING OSTEOPOROSIS AND HORMONAL IMBALANCE

[75] Inventor: Marcus G. Grodberg, Newton, Mass.

[73] Assignee: Colgate - Palmolive Company, New York, N.Y.

[21] Appl. No.: 519,088

[22] Filed: May 4, 1990

[51] Int. Cl.$^5$ .................. A61K 9/22; A61K 9/26; A61K 7/18; A61K 33/16
[52] U.S. Cl. .................. 514/171; 424/468; 424/469; 424/470; 424/494; 424/495; 424/676; 424/52; 519/781
[58] Field of Search .............. 424/52, 468, 469, 470, 424/494, 495, 676; 514/781, 171

[56] References Cited

U.S. PATENT DOCUMENTS

| | | | |
|---|---|---|---|
| 4,101,668 | 1/1978 | Samour | 514/419 |
| 4,125,621 | 11/1978 | Samour | 514/419 |
| 4,185,108 | 1/1980 | Samour | 514/419 |
| 4,220,552 | 9/1980 | Hitchcock | 424/52 |
| 4,726,952 | 2/1988 | Walsdorf et al. | 424/676 |
| 4,728,513 | 3/1988 | Ventovras | 424/676 |
| 4,795,644 | 1/1989 | Zentner et al. | 424/468 |
| 4,814,183 | 3/1989 | Zentner et al. | 424/485 |
| 4,851,228 | 7/1989 | Zentner et al. | 424/456 |
| 4,859,467 | 8/1989 | Grodberg et al. | 424/676 |
| 4,861,590 | 8/1989 | Grodberg | 424/606 |

FOREIGN PATENT DOCUMENTS

| | | |
|---|---|---|
| 213083 | 3/1987 | European Pat. Off. |
| 2630326 | 1/1978 | Fed. Rep. of Germany |
| 2922671 | 12/1980 | Fed. Rep. of Germany |
| 3514583 | 10/1985 | Fed. Rep. of Germany |
| 3727616 | 3/1988 | Fed. Rep. of Germany |
| 2542199 | 9/1984 | France |

*Primary Examiner*—Shep K. Rose
*Attorney, Agent, or Firm*—Murray M. Grill; Robert L. Stone

[57] ABSTRACT

A medication for providing fluoride ion for the prevention and treatment of bone loss disease, together with an estrogen-containing substance for not only treating hormonal imbalance but to obtain more advantageous use of the fluoride ion within the body. The dosage is a lozenge, tablet or capsule containing from 20 to 100 milligrams of sodium monofluorophosphate and further including an estrogen-containing substance and a slow release mechanism for controlling release of the fluoride ion and estrogen over a period of from four to eight hours after swallowing. Up to ten percent of sodium fluoride and/or calcium can be added.

9 Claims, No Drawings

COMPOSITION FOR TREATING OSTEOPOROSIS AND HORMONAL IMBALANCE

BACKGROUND OF THE INVENTION

1. Field of the Invention

This invention relates to a sustained release systemic fluoride drug product for treatment or prevention of osteoporosis or other bone disease. More particularly, this invention relates to the use of sodium monofluorophosphate, alone or in combination with another fluorine compound, together with an estrogen-containing substance and, if desired, a calcium containing substance, in a sustained release solid unit dosage form, suitable for use in the treatment and prevention of osteoporosis, alveolar bone loss or other bone diseases where systemic fluoride ion is efficacious and further treating hormonal imbalance and enhancing utilization of the fluoride ion by introduction of estrogen.

2. Description of the Prior Art

Fluoride stimulates the activity of bone-forming cells and, together with calcium and phosphate, the two major mineral components of bone is also stored in the bone structure. Fluoride seems to directly stimulate the proliferation of osteoblasts resulting in an increase in bone formation.

U.S. Pat. No. 3,287,219 discloses the oral administration of sodium fluoride to promote bone healing.

The role of fluoride in strengthening the teeth and in imparting acid resistance and preventing caries in dental treatment is well documented. The use of sodium fluoride tablets and liquids for infants and young children in areas where the drinking water is not or is only insufficiently fluoridated is well known. For this purpose, fluoride ion from NaF is administered in dosages of about 0.25 to about 1 mg per day. Representative patents in this area include U.S. Pat. Nos. 3,306,824, 4,265,877 and 4,397,837 (toothpaste). The use of sodium monofluorophosphate (MFP) in dental products, particularly toothpaste products, as an anticaries fluoride additive is also well known and is mentioned in U.S. Pat. No. 4,397,837, cited above. The MFP is slowly metabolized by an intestinal enzyme, MFPase or alkaline phosphatase into free fluoride ion which, in turn, is absorbed into the blood stream, some of the MFP being directly absorbed in the liver and converted therein to F ion.

More recently, the use of NaF or MFP for the treatment of bone disease to promote bone formation and strengthen bone has received wide attention. In fact, although not yet approved for use in the United States, both NaF and MFP products for the treatment and prevention of osteoporosis are available in Europe. Thus, Flurexal® is an enteric coated tablet containing 22 mg sodium fluoride (10 mgF) sold by Zyma SA Nyon Suisse; Tridin® is a chewable tablet containing 38 mg sodium monofluorophosphate (5 mg F), 500 mg calcium gluconate monohydrate, 500 mg calcium citrate tetrahydrate, 200 mg carboxymethyl cellulose, available from Opfermann Arzneimittel GmbH.

According to the directions for use provided with the medications, Flurexal® should be taken three times each day, while Tridin® should be taken one to two tablets three times a day for treatment or one tablet three times a day for prevention of steriod-osteoporosis. In general, the typical recommended dosage for F ion is in the order of from about 20 to 50 mg per day for a human adult.

The literature provided with Tridin® states that gastric and intestinal irritation is seldom observed. To the same effect, Yngve Ericsson, "Monofluorophosphate Physiology: General Considerations," Caries Res. 17 (Suppl. 1), pages 46–55 (1983), reported that "neither in patients nor in numerous experiments with laboratory workers has any subjective discomfort been recorded with doses up to 30 mg F as MFP." However, as discussed in U.S. Pat. Nos. 4,859,467 and 4,861,590 to Baylink and Grodberg, gastric and intestinal distress is in fact a significant occurrence.

Attempts to solve the adverse side effects of gastrointestinal (GI) tract symptoms by minimizing the availability of F ion in the stomach by providing NaF in a sustained release form have only been partially effective in avoiding GI irritation. More particularly, it has been observed that, while slow release sodium fluoride is well tolerated by approximately 70% of patients, there is adverse gastrointestinal effects in the other approximate 30% of patients.

SUMMARY OF THE INVENTION

The present invention provides a fluoride treatment for osteoporosis, alveolar bone loss and other localized bone disorders which virtually solves the problem of gastric irritation, together with treatment of hormonal imbalance.

Quite surprisingly, in view of the fact that the sustained release type unitary dosage product for administering NaF is only variably effective in avoiding the occurrence of gastric irritation, it has now been discovered that, when MFP is administered in a sustained release form, the occurrence of gastrointestinal irritation is almost totally eliminated. Further, in the same dosage when an estrogen-containing substance is added, minimal side effects are noticed, while utilization of the fluoride ion is especially enhanced.

Accordingly, it is an object of this invention to provide a fluoride ion and estrogen-containing substance drug preparation useful in the treatment or prevention of osteoporosis (bone disease) and hormonal imbalance which does not cause adverse GI symptoms, such as gastric irritation.

It is a specific object of this invention to provide a unitary dosage form of MFP and estrogen which provides sufficient quantities of F ion and estrogen to be useful in the prevention or treatment of osteoporosis and hormonal imbalance in which the MFP and estrogen is administered from the unitary dosage product at a slow rate over the course of at least several hours, preferably a maximum of eight hours, whereby occurrence of gastric irritation is avoided.

It is another object of the invention to provide a method for treating or preventing osteoporosis by administering, at least once daily, to a patient suffering from or at risk for osteoporosis a solid unitary dosage product containing sufficient amounts of MFP and estrogen effective for the promotion of, or maintenance of, formation and strengthening for diseased or weakened bone wherein the product includes means for slowly releasing the MFP and estrogen over the course of at least several hours to a maximum of eight hours whereby the estrogen not only treats hormonal imbalance, but enhances the utilization of the fluoride ion.

In accordance with these objectives and other objects, which will become apparent from the following description, the present invention provides, in one aspect thereof, a medication for providing fluoride ion for the treatment or prevention of osteoporosis or other bone disease, including alveolar bone loss and hormonal imbalance, which is in the form of a solid unitary dosage tablet or capsule containing from about 20 milligrams (mg) to about 100 mg of sodium monofluorophosphate ($Na_2PO_3F$) and including 0.02 mg to 1.0 mg of an estrogen-containing substance and further including means for controlling the release of the monofluorophosphate over a period preferably from four up to eight hours whereby the quantity of fluoride ion and estrogen present in the stomach at any given time is below the threshhold value at which gastric irritation will occur.

The sustained release unitary dosage product of this invention may include MFP and estrogen as the active ingredients. Alternatively, MFP may be used in combination with NaF, or a mixture thereof with or without a calcium containing substance and/or a phosphate containing substance.

In a specific and preferred embodiment of the invention, the means for controlling release of MFP and estrogen and any other active ingredient includes a mass of water swellable cellulosic powder forming a coherent fibrous powder network as a matrix in which the monofluorophosphate and estrogen is uniformly and homogeneously dispersed, whereby, upon introduction of the unitary dosage product into an aqueous medium, the cellulosic fibers at the surface of the product soften and loosen from the remaining mass of fibers to thereby release a stream of the monofluorophosphate and estrogen.

The initial loosening of the fibers causes a delay in the release of the fluoride ion and estrogen or a very slow release thereof for the first one to three hours, allowing the dosage to pass through the stomach and into the intestinal tract before the uniform release of the fluoride ion and estrogen occurs.

According to the method aspect of the invention, a patient suffering from or at risk of osteoporosis and hormonal imbalance is treated with at least one of the sustained release unitary dosage MFP and estrogen products of this invention along or with a calcium ion supplement.

DETAILED DESCRIPTION OF THE INVENTION

Osteoporosis can be broadly defined as increasing weakness and fragility of the bones. It most frequently occurs in elderly, post-menopausal women and in elderly (presenile or senile) men, but also occurs in idiopathic forms. Osteoporosis can also occur in connection with, i.e. as an undesirable side effect of, corticoid treatment (steriod-osteoporosis). Certain localized forms of bone disease may also be associated with a general weakness and fragility of the bone structure due to insufficient new bone formation. Therapeutic indications includes any bone wasting disease, genetic, such as osteogenesis imperfecta, or acquired, such as renal bone disease.

In women undergoing menopause and post-menopausal females there is often present an hormonal imbalance heretofore treated by oral dosages of estrogen or by injection of estrogen.

One of the effects of advanced periodontal disease is the loss of alveolar bone (i.e. that portion of the jaw bones that support the teeth) mass, which eventually causes loosening and loss of teeth. Alveolar bone loss may also occur after tooth extractions and, in some cases, after the insertion of dental implants.

Bone is composed of an organic phase, collagen and an inorganic crystalline phase of calcium phosphate, or more specifically, hydroxyapatite, $Ca_{10}(PO_4)_6(OH)_2$. Fluoride plays an important role in the prevention of bone loss by stimulating the formation of less soluble fluorapatite $Ca_{10}(PO_4)_6F_2$. Therefore, in osteoporosis, alveolar bone loss and other bone diseases associated with general weakening or loss of the bone tissue, or in cases where the normal dietary intake of calcium is insufficient, a dietary supplement to supply additional calcium is usually appropriate. The addition to the calcium supplement of, or the separate administration of, a source of fluoride ion will, according to recent scientific research, greatly enhance the reversal of bone loss, the fluoride stimulating new bone formation and the calcium being an indispensable building block for bone tissue.

Sodium fluoride and sodium monofluorophosphate can each be used to provide the fluoride ion to be absorbed into the blood for eventual skeletal uptake. Sodium fluoride, NaF, has the advantage that it has a higher F content than sodium monofluorophosphate, MFP. NaF is also more rapidly absorbed, at least in the first few hours, into the blood. However, NaF has higher acute toxicity than MFP and causes stomach irritation in a much higher percentage of patients than does MFP. Moreover, and perhaps most important, is the fact that NaF is incompatible with ionizable calcium compounds, forming poorly soluble $CaF_2$, thereby depleting the availability of the F ion to a large extent and of the Ca ion to a smaller extent (based on the much greater total quantity of calcium present in the patient's system). On the other hand, MFP is compatible with ionizable calcium compounds since Ca(MFP) is about twenty times more soluble than $CaF_2$.

Unfortunately, when ingested orally in the recommended dosages, typically about 20 to 50 mg F per day for human adults, MFP, although not as pronounced as NaF, also causes stomach irritation.

In accordance with the present invention, it has been found that by incorporating the MFP alone or in combination with a small amount of sodium fluoride, the occurrence of GI irritation can be avoided. Although not wishing to be bound by any particular theory, it is presumed that, by only gradually releasing the MFP from the unitary dosage product, the quantity of fluoride ion present in the stomach at any given time is below the threshhold value at which gastrointestinal irritation will occur. Since a similar alleviation of GI symptoms is not observed for a slow release NaF product, it is further presumed that the more rapid ionization of NaF into sodium and fluorine ions, as compared to the rate of enzymatic hydrolysis of MFP in the stomach, may also account for this different result. In any case, by whatever mode of action, by incorporating the MFP with means for controlling the release of the monofluorophosphate over a period extending up to a maximum of eight hours from the time of ingestion, gastrointestinal irritation will be avoided. Gastrointestinal irritation from the intake of an estrogen-containing substance is also minimized.

The means for providing controlled (i.e. sustained) release of the active ingredients may be selected from any of the known sustained-release oral drug delivery systems. Some of the known sustained-release delivery systems for controlling the release of an active ingredient over a course of about four or more hours include the wax matrix system, the coated granular system, the "miniature osmotic pump" system and the Forest Synchron system (of Forest Laboratories).

The wax matrix system disperses the active ingredient(s) in a wax binder which slowly dissolves in body fluids to gradually release the active ingredient(s).

The coated granular system encapsulates the active ingredient(s) in various polymeric coatings that have varying degrees of solubility dependent upon pH and/or enzymes to vary the drug release rate from the respective granules. A multiplicity of granules is filled into a gelatin or similar water-soluble capsule.

In the miniature osmotic "pump," an active ingredient is coated with a semipermeable membrane. The pump works when water-soluble drugs are released through a hole drilled into the membrane.

The preferred controlled-release oral drug delivery system is the Forest Synchron drug delivery system in which the active ingredient, MFP, is dispersed uniformly and homogeneously throughout a mass of water-swellable modified cellulosic powder or fibers forming a coherent network, as a matrix. The mixture of the fibrous or powdery mass and active ingredient(s), with optional additives, such as flavoring, binder, lubricant, processing aids and the like, is compacted into a tablet which, prior to use, is hard and dry. After the tablet is swallowed and comes into contact with the aqueous stomach and intestinal fluids, the outer layer of the tablet becomes soft and gelatinous, while the inner portions remain dry. At the softened and gelatinous surface, the cellulose powder or fibers become loose and separate from the remaining mass, thereby releasing a portion of the active ingredients. During the period the tablet remains in the stomach and then travels down through the GI tract, the newly exposed outer surfaces become moistened and in turn become soft and gelatinous to loosen additional cellulosic material, thereby allowing additional amounts of MFP, estrogen and any dispersed substances to be steadily and generally uniformly released into the stomach or intestines. By the time the tablet has passed through the GI tract, after about four to eight hours, the tablet is completely dissipated and dissolved. Accordingly, the ingested tablet will release a stream of the sodium monofluorophosphate and estrogen, as well as any other active ingredient.

Typical formulations of a sustained-release unitary dosage tablet according to the invention which utilizes the Forest Synchron system is shown immediately below:

EXAMPLE 1

| Ingredient | Amount (milligrams) |
| --- | --- |
| Na2 FPO3 | 76.0 |
| Ethyl Cellulose | 8.0 |
| Hydroxypropylmethylcellulose (Methocel E4M) | 7.0 |
| Hydrogenated Vegetable Oil | 1.0 |
| Sodium salt of naphthalenesulfonic acid-formaldehyde condensate (Tamol N) | 1.0 |
| Conjugated Estrogen USP | .5 |
| Total Content weight | 93.5 mg |

The amount of conjugated estrogens USP may vary from 0.3 to 0.625 mg.

EXAMPLE 2

In lieu of conjugated estrogens USP, esterified estrogens USP in an amount varying from 0.2 to 0.4 mg may be employed, preferably 0.3 mg. As a result, not only is hormonal imbalance treated, but the estrogen has the additional effect of enhancing utilization of the fluoride ion.

EXAMPLE 3

In lieu of the conjugated estrogens USP in Example 1, there is utilized estradiol and derivatives USP in an amount varying from 0.02 to 0.2 mg, preferably 0.1 mg. As a result, not only is hormonal imbalance treated, but the estrogen has the additional effect of enhancing utilization of the fluoride ion.

These formulations provide 10 mg F ion as MFP and estrogen and are designed to release the MFP in the gastrointestinal tract slowly from four to eight hours after ingestion.

The amount of MFP can generally be varied over a range of from about 20 mg to about 100 mg MFP per tablet (or pill, capsule, etc.) to provide correspondingly from about 2.5 mg to about 13 mg F per tablet. Therefore, based on the current recommended dosage for treatment for osteoporosis and related bone diseases, or from about 30 to 60 mg F per day and recommended dosages of, at most, about one-half these levels for prevention of osteoporosis in, for example, postmenopausal women and presenile or senile men, or for prevention of steriod-osteoporosis or alveolar bone loss, total daily dosages of one or two tablets two to four times a day will provide the total recommended requirement of fluoride, as well as estrogen.

The use of sodium monofluorophosphate as the sole fluoride source is preferred. However, if desired, the formulations can include small amounts of NaF in amounts up to about ten percent (10%), such as 5 to 10%, by weight based on the total weight of NaF+MFP can be added to a sustained-release medication. It has been found that the administration of NaF unexpectedly increases alkaline phosphatase enzyme levels in the intestines, thereby enhancing the formulation of F from MFP.

In addition to each of the above Examples, other active ingredients may be included which are as follows:

Calcitriol, 1.25— Dihydroxyvitamin $D_3$ form, in a daily dosage in the range of 0.25 to 0.50 mcg.

Phosphates, Potassium and Sodium Mono- and Dibasic Phosphates (250 mg P per tablet) form, in a daily dosage in the range of 250 to 500 mg P qid.

What is claimed is:

1. A medication for providing fluoride ion for the treatment and prevention of bone loss disease including osteoporosis, alveolar bone loss and hormonal imbalance, which comprises a solid, unitary dosage tablet, lozenge or capsule containing from about 20 to 100 milligrams of sodium monofluorophosphate and 0.02 to 1.2 mg of an estrogen-containing substance, uniformly and homogeneously dispersed in a hard dry compacted mass of water-swellable powders or fibers or cellulose material forming a coherent network as matrix which softens and loosens, from the remaining mass, upon introduction into an aqueous medium, to thereby release a stream of the uniformly and homogeneously dispersed fluoride and estrogen, for controlling the release of the monofluorophosphate over a period extending from four up to eight hours after swallowing, whereby the quantity of fluoride ions at any given time is below the threshhold value at which gastric irritation will occur.

2. The composition of claim 1, wherein said estrogen-containing substance is selected from the group consisting of conjugated estrogens USP, esterified estrogens USP, estradiol and derivatives USP.

3. The composition of claim 1, which further comprises up to about 10% by weight of sodium fluoride based on the combined weight of sodium monofluorophosphate and sodium fluoride.

4. The composition of claim 1, wherein the means for controlling release of the monofluorophosphate comprises a mass of water-swellable ethyl cellulose and hydroxypropyl methyl cellulose powder or fiber forming a coherent network as a matrix in which the monofluorophosphate is uniformly and homogeneously dispersed, whereby, upon introduction of the unitary dosage into an aqueous medium, the ethyl cellulose and hydroxypropyl methyl cellulose powder or fibers at the surface of the unitary dosage soften and loosen from the remaining mass to thereby release a stream of the monofluorophosphate and estrogen-containing substance.

5. The composition of claim 4, which further comprises sodium fluoride in an amount up to about 10% by weight based on the combined weight of sodium monofluorophosphate and sodium fluoride.

6. The composition of claim 4, wherein the estrogen-containing substance is from 0.3 to 0.625 mg of conjugated estrogens USP.

7. The composition of claim 4, wherein the estrogen-containing substance is from 0.2 to 0.4 mg of esterified estrogens USP.

8. The composition of claim 4, wherein the estrogen-containing substance is from 0.02 to 0.2 mg of estradiol and derivatives USP.

9. The composition of claim 1, further including as active ingredients one or more of calcium, vitamin $D_3$ and phosphates.

* * * * *